US007860300B2

(12) United States Patent
Siltanen et al.

(10) Patent No.: US 7,860,300 B2
(45) Date of Patent: Dec. 28, 2010

(54) METHOD AND SYSTEM FOR DETERMINING A SHARP PANORAMIC IMAGE CONSTRUCTED FROM A GROUP OF PROJECTION IMAGES

(75) Inventors: Samuli Siltanen, Helsinki (FI); Martti Kalke, Tuusula (FI); Henri Setälä, Järvenpää (FI); Esa Suuronen, Kerava (FI)

(73) Assignee: PaloDEx Group Oy (FI)

( * ) Notice: Subject to any disclaimer, the term of this patent is extended or adjusted under 35 U.S.C. 154(b) by 1022 days.

(21) Appl. No.: 11/207,165

(22) Filed: Aug. 18, 2005

(65) Prior Publication Data

US 2007/0041489 A1 Feb. 22, 2007

(51) Int. Cl.
*G06K 9/00* (2006.01)

(52) U.S. Cl. .................. 382/154; 382/224; 709/200

(58) Field of Classification Search ................. 382/154, 382/131, 132; 378/4, 40
See application file for complete search history.

(56) References Cited

U.S. PATENT DOCUMENTS

| 4,418,419 | A | * | 11/1983 | Schreiber et al. ............. 378/40 |
| 4,624,007 | A | * | 11/1986 | Muranushi ..................... 378/4 |
| 4,649,555 | A | * | 3/1987 | Matsubayashi ................. 378/4 |
| 4,856,038 | A | | 8/1989 | Guenther et al. |
| 5,195,114 | A | * | 3/1993 | Sairenji et al. ................ 378/40 |
| 6,493,415 | B1 | * | 12/2002 | Arai et al. ....................... 378/4 |
| 2001/0021244 | A1 | | 9/2001 | Suzuki et al. |
| 2002/0168579 | A1 | * | 11/2002 | Suzuki et al. .................. 430/7 |
| 2003/0069134 | A1 | * | 4/2003 | Shimomura et al. ......... 503/227 |
| 2004/0000630 | A1 | * | 1/2004 | Spartiotis et al. ......... 250/208.1 |

OTHER PUBLICATIONS

Finnish Search Report for corresponding Finnish Patent Application No. 20060732, dated May 11, 2007.

\* cited by examiner

*Primary Examiner*—Daniel G Mariam
*Assistant Examiner*—Aklilu K Woldemariam
(74) *Attorney, Agent, or Firm*—Andrus, Sceales, Starke & Sawall, LLP

(57) ABSTRACT

The invention relates to a method and system for determining a sharp panoramic image constructed from a group of projection images, especially the invention relates to defining a structure of the panoramic X-ray image of an area of a dentition and of jaws. The structure of a panoramic image to be generated from a group of projection images is determined by at least two crucial parameters, namely parameters of the central surface S of the sharp layer and thickness t(s) of the sharp layer, using penalty function F(S,t), which is at least a penalty function F3(S,t) of low-frequency changes in the computed panoramic image corresponding to the choices S and t(S). After computing F3(S,t) the best center surface and thickness function (in other words the sharpest layer of the panoramic image) is obtained by minimizing said penalty function F(S,t) over parameter space.

29 Claims, 2 Drawing Sheets

METHOD AND SYSTEM FOR DETERMINING A SHARP PANORAMIC IMAGE CONSTRUCTED FROM A GROUP OF PROJECTION IMAGES

TECHNICAL FIELD OF THE INVENTION

The invention relates to a method and system for determining a sharp panoramic image constructed from a group of projection images. Especially the invention relates to defining a structure of the panoramic X-ray image of an area of a dentition and of jaws.

BACKGROUND OF THE INVENTION

Extra oral/panoramic dental imaging is nowadays a very common practise in a medical treatment of patients. Typical X-ray apparatus used for extra oral/panoramic dental imaging includes a rotative arm suspended at one end of a support column and an X-ray generating device and an X-ray detecting device (C-arm) oppositely fixed to respective ends of the rotative arm. The X-ray detecting device (C-arm) is typically a film-based device or CCD-based (Charged Coupled Device) device. The X-ray exposure is performed with rotation of the arm so that the movements of the rotative arm and thus also movements of the X-ray generating device and the X-ray detecting device are synchronized in such a way that an image of an area of desired shape, for example the patient's dental arch, is obtained on the film or CCD-device.

In panoramic X-ray imaging it is known, in order to obtain a sharp image of the dental arch, to allow the rotational axis of the support arm to move during the exposure in a predetermined manner linearly or non-linearly in such a way that this movement is dependent on the angular position of the support arm at each given time. The movement of the rotational axis may be linear, and parallel to the axis of symmetry of the dental arch, perpendicular to it, curved, or non-continuous between predetermined points.

In order to obtain a certain sharp panoramic image layer of an object to be determined it is very important to position the object accurately to the correct place in relation to the imaging apparatus. If another panoramic layer is desired as a sharp layer, either the imaging apparatus or the object to be determined must be shifted or repositioned. In practice the shifting and repositioning of the object is always cumbersome and time-consuming. Furthermore, the known X-ray photography apparatus do not always provide so extensive possibilities for positioning and use as are generally desired in order to obtain a precise image of some specific area or part of an area.

SUMMARY OF THE INVENTION

The object of the invention is to provide a method and system to determine an arbitrary sharp panoramic image layer in an image constructed from a group of projection images, where the desired layer for the panoramic image can be determined after obtaining projection image data of the object, and furthermore to allow the positioning of the object to be determined more freely and still obtain sharp panoramic layer images. Especially the object of the invention is to allow generate numbers of sharp panoramic image layers from data obtained from the object by only one shot.

The object of the invention is fulfilled by defining the structure of a panoramic image to be generated from a group of projection images by at least two crucial parameters, namely parameters of the central surface S of the sharp layer and thickness t(s) of the sharp layer, using penalty function $F(S,t)$, which is a sum of one or more of the following terms 1) penalty function of changes in the surface s, 2) penalty function of changes in the thickness function t(S), and 3) penalty function of low-frequency changes in the computed panoramic image corresponding to the choices S and t(S), and after which the best center surface and thickness function (in other words the sharpest layer of the panoramic image) is obtained by minimizing said penalty function $F(S,t)$ over parameter space. The utilization of the invention is not restricted to the penalties mentioned in this patent application but the penalty function may contain other penalties.

It should be noted that the sharp panoramic image layer can be obtained according to the present invention from image data using only term F3 in the penalty function.

The point is that F gives high penalty for panoramic images that do not show clearly the desired diagnostic information.

It is characteristic for the method of the invention for determining a sharp panoramic image layer constructed from a group of projection images comprising at least following steps:

defining the structure of the panoramic image by at least two crucial parameters, the first parameter relating to the central surface S of the sharp layer and the second parameter relating to the thickness t(s) of the sharp layer, using a penalty function $F(S,t)$ to obtain the best choice for a center surface and thickness function by minimizing said penalty function $F(S,t)$ over parameter space, where said penalty function $F(S,t)$ is sum of $F3(S,t)$, and $F3(S,t)$ computes first the panoramic image corresponding to the choices S and t(S) given as argument, and penalizes low-frequency images more than high-frequency images of said computed panoramic image.

It is also characteristic for the method of the invention for determining a sharp panoramic image layer constructed from a group of projection images comprising at least following steps:

defining the structure of the panoramic image by at least two crucial parameters, the first parameter relating to the central surface S of the sharp layer and the second parameter relating to the thickness t(s) of the sharp layer, using a penalty function $F(S,t)$ to obtain the best choice for a center surface and thickness function by minimizing said penalty function $F(S,t)$ over parameter space, where said penalty function $F(S,t)$ is sum of $F1(S)$ and $F3(S,t)$, where 1) $F1(S)$ penalizes changes in the surface S, and
2) $F3(S,t)$ computes first the panoramic image corresponding to the choices S and t(S) given as argument, and penalizes low-frequency images more than high-frequency images of said computed panoramic image.

It is also characteristic for the method of the invention for determining a sharp panoramic image layer constructed from a group of projection images comprising at least following steps:

defining the structure of the panoramic image by at least two crucial parameters, the first parameter relating to the central surface S of the sharp layer and the second parameter relating to the thickness t(s) of the sharp layer, using a penalty function $F(S,t)$ to obtain the best choice for a center surface and thickness function by minimizing said penalty function $F(S,t)$ over parameter space, where said penalty function $F(S,t)$ is sum of $F2(t)$ and $F3(S,t)$, where 1) $F2(t)$ penalizes changes in the thickness function t(S), and 2) F3(S,t) computes first the panoramic image corresponding to the choices S and t(S) given as arguments and penalizes low-frequency images more than high-frequency images of said computed panoramic image.

It is also characteristic for the method of the invention for determining a sharp panoramic image layer constructed from a group of projection images comprising at least following steps:

defining the structure of the panoramic image by at least two crucial parameters, the first parameter relating to the central surface S of the sharp layer and the second parameter relating to the thickness t(s) of the sharp layer, using a penalty function F(S,t) to obtain the best choice for a center surface and thickness function by minimizing said penalty function F(S,t) over parameter space, where said penalty function F(S,t) is sum of F1(S), F2(t) and F3(S,t), where 1) F1(S) penalizes changes in the surface S,
2) F2(t) penalizes changes in the thickness function t(S), and
3) F3(St) computes first the panoramic image corresponding to the choices S and t(S) given as argument, and penalizes low-frequency images more than high-frequency images of said computed panoramic image.

It is characteristic for the system of the invention for determining a sharp layer in a panoramic image constructed from group of projection images comprising at least following:

means for defining the structure of the panoramic image by at least two crucial parameters, the first parameter relating to the central surface S of the sharp layer and the second parameter relating to the thickness t(s) of the sharp layer, means for using a penalty function F(S,t) to obtain the best choice for a center surface and thickness function by minimizing said penalty function F(S,t) over parameter space, where said penalty function F(S,t) is F3(S,t), and F3(S,t) computes first the panoramic image corresponding to the choices S and t(S) given as argument, and penalizes low-frequency images more than high-frequency images of said computed panoramic image.

It also is characteristic for the system of the invention for determining a sharp layer in a panoramic image constructed from group of projection images comprising at least following:

a means for defining the structure of the panoramic image by at least two crucial parameters, the first parameter relating to the central surface S of the sharp layer and the second parameter relating to the thickness t(s) of the sharp layer, means for using a penalty function F(S,t) to obtain the best choice for a center surface and thickness function by minimizing said penalty function F(S,t) over parameter space, where said penalty function F(S,t) is sum of F1(S) and F3(S,t), where 1) F1(S) penalizes changes in the surface S, and
2) F3(S,t) computes first the panoramic image corresponding to the choices S and t(S) given as argument, and penalizes low-frequency images more than high-frequency images of said computed panoramic image.

It is also characteristic for the system of the invention for determining a sharp layer in a panoramic image constructed from group of projection images comprising at least following:

means for defining the structure of the panoramic image by at least two crucial parameters, the first parameter relating to the central surface S of the sharp layer and the second parameter relating to the thickness t(s) of the sharp layer, means for using a penalty function F(S,t) to obtain the best choice for a center surface and thickness function by minimizing said penalty function F(S,t) over parameter space, where said penalty function F(S,t) is sum of F2(t) and F3(6,t), where 1) F2(t) penalizes changes in the thickness function t(S), and
2) F3(S,t) computes first the panoramic image corresponding to the choices S and t(S) given as argument, and penalizes low-frequency images more than high-frequency images of said computed panoramic image.

It is also characteristic for the system of the invention for determining a sharp layer in a panoramic image constructed from group of projection images comprising at least following:

means for defining the structure of the panoramic image by at least two crucial parameters, the first parameter relating to the central surface S of the sharp layer and the second parameter relating to the thickness t(s) of the sharp layer, means for using a penalty function F(S,t) to obtain the best choice for a center surface and thickness function by minimizing said penalty function F(S,t) over parameter space, where said penalty function F(S,t) is sum of F1(S), F2(t) and F3(S,t), where 1) F1(S) penalizes changes in the surface S,
2) F2(t) penalizes changes in the thickness function t(S), and
3) F3(S,t) computes first the panoramic image corresponding to the choices S and t(S) given as argument, and penalizes low-frequency images more than high-frequency images of said computed panoramic image.

It is characteristic for the computer program product of the invention for determining a sharp layer in a panoramic image constructed from group of projection images comprising at least following:

said computer program product comprises defining code means, which is adapted to define the structure of the panoramic image by at least two crucial parameters, the first parameter relating to the central surface S of the sharp layer and the second parameter relating to the thickness t(s) of the sharp layer, when said defining code means is run on a data processing unit, said computer program product comprises penalty function code means, which is adapted to determine a penalty function F(S,t) to obtain the best choice for a center surface and thickness function by minimizing said penalty function F(S,t) over parameter space, where said penalty function F(S,t) is F3(S,t), and F3(S,t) computes first the panoramic image corresponding to the choices S and t(S) given as argument, and penalizes low-frequency images more than high-frequency images of said computed panoramic image, when said penalty function code means is run on a data processing unit.

In one example, it is characteristic for the computer usable medium to be adapted to determine a sharp layer in a panoramic image constructed from group of projection images, when said computer program product is run on a data processing unit.

It is also characteristic for the computer program product of the invention for determining a sharp layer in a panoramic image constructed from group of projection images comprising at least following:

said computer program product comprises defining code means, which is adapted to define the structure of the panoramic image by at least two crucial parameters, the first parameter relating to the central surface S of the sharp layer and the second parameter relating to the thickness t(s) of the sharp layer, when said defining code means is run on a data processing unit, said computer program product comprises penalty function code means, which is adapted to determine a penalty function F(S,t) to obtain the best choice for a center surface and thickness function by minimizing said penalty function F(S,t) over parameter space, where said penalty function F(S,t) is sum of F1(S) and F3(S,t), where
1) F1(S) penalizes changes in the surface S, and
2) F3(S,t) computes first the panoramic image corresponding to the choices S and t(S) given as argument, and penalizes low-frequency images more than high-frequency images of said computed panoramic image, when said penalty function code means is run on a data processing unit.

In one example, it is also characteristic for the computer usable medium comprising computer program product to be adapted to determine a sharp layer in a panoramic image constructed from group of projection images, when said computer program product is run on a data processing unit.

It is also characteristic for the computer program product of the invention for determining a sharp layer in a panoramic image constructed from group of projection images comprising at least following:

said computer program product comprises defining code means, which is adapted to define the structure of the panoramic image by at least two crucial parameters, the first parameter relating to the central surface S of the sharp layer and the second parameter relating to the thickness t(s) of the sharp layer, when said defining code means is run on a data processing unit, said computer program product comprises penalty function code means, which is adapted to determine a penalty function F(S,t) to obtain the best choice for a center surface and thickness function by minimizing said penalty function F(S,t) over parameter space, where said penalty function F(S,t) is sum of F2($t$) and F3(S,t), where
1) F2($t$) penalizes changes in the thickness function t(S), and
2) F3(S,t) computes first the panoramic image corresponding to the choices S and t(S) given as argument, and penalizes low-frequency images more than high-frequency images of said computed panoramic image, when said penalty function code means is run on a data processing unit.

In one example, it is also characteristic for the computer usable medium comprising computer program product to be adapted to determine a sharp layer in a panoramic image constructed from group of projection images, when said computer program product is run on a data processing unit.

It is also characteristic for the computer program product of the invention for determining a sharp layer in a panoramic image constructed from group of projection images comprising at least following;

said computer program product comprises defining code means, which is adapted to define the structure of the panoramic image by at least two crucial parameters, the first parameter relating to the central surface S of the sharp layer and the second parameter relating to the thickness t(s) of the sharp layer, when said defining code means is run on a data processing unit, said computer program product comprises penalty function code means, which is adapted to determine a penalty function F(S,t) to obtain the best choice for a center surface and thickness function by minimizing said penalty function F(S,t) over parameter space, where said penalty function F(S,t) is sum of F1(S), F2($t$) and F3(S, t), where
1) F1(S) penalizes changes in the surface S,
2) F2($t$) penalizes changes in the thickness function t(S), and
3) F3(S,t) computes first the panoramic image corresponding to the choices S and t(S) given as argument, and penalizes low, frequency images more than high-frequency images of said computed panoramic image, when said penalty function code means is run on a data processing unit.

In one example, it is also characteristic for the computer usable medium comprising computer program product to be adapted to determine a sharp layer in a panoramic image constructed from group of projection images, when said computer program product is run on a data processing unit.

According to an embodiment of the present invention a group of projection images from an object to be determined is obtained advantageously in a digital form. The projection images may be obtained for example by X-ray imaging devices known from the prior art. The object is typically a patient and the area to be determined by the present invention is most advantageously the area of a dentition and of jaws.

In the imaging process number of single projection images are taken in a short time so that typical rate may be for example 100 images in one second. Moreover images are taken in such a way that each image is at least partly overlapped with its nearest image. The displacement between the adjacent images is typically 1 pixel or 0.1 millimeter, but it should be clear to a skilled person that the displacement can also be greater.

After obtaining the group of projection images the panoramic image can be constructed of said projection images for example by methods known from a prior art. According to the present invention two crucial parameters are used to define the structure of a panoramic image. The first parameter is the center surface S of the sharp layer, and the second is thickness t(s) of the sharp layer given advantageously in millimeters at each point s of S.

Thickness t(s) varies smoothly as a function of s, typical values being between 2 mm and 30 mm.

In the present invention, the surface S is represented in parametric form: S(p1, p2, . . . , pN), where p1, p2, . . . , pN are real valued parameters. For example, the parameters can be the coordinates of a collection of control points (x1, y1, z1), (x2, y2, z2), . . . , (xM, yM, zM) in a three dimensional space, and the surface S is made up of spline functions passing through the control points. The parameter values are limited advantageously from above and below in such a way that for all possible choices of the parameters, the corresponding surface S can be realized with the panoramic X-ray device used in the invention.

The thickness function t(s) is parameterized similarly to the parameterization of S: write t(s1, s2, ..., sK), where s1, s2, ..., sK is a collection of points on the surface S.

Once the parameterizations of S and t(s) are chosen, the best choice for a center surface of a sharp layer is automatically determined (an initial assumption for the best and thus the sharpest panoramic layer) by defining a penalty function F(S,t). The penalty function F(S,t) is defined by taking a surface S and a thickness function t as argument and returning a non-negative real number. The value F(S) is described by a sum of non-negative penalties, such as for example F(S,t)=F1(S)+F2(t)+F3(S,t), where F1(S) penalizes changes in the surface S (advantageously high-frequency changes in the surface S preferring a smooth curve in the direction of the surface), F2(t) penalizes changes in the thickness function t (advantageously high-frequency changes in the thickness function t preferring a smooth curve in the direction of a thickness), and F3(S,t) computes first the panoramic images corresponding to the choices S and t given as argument, and penalizes lows frequency images more than high-frequency images. In other words, F3 favors choices of S and t leading to sharp panoramic images (penalizing low-frequency components, or blurred areas).

However, it should be noted, that F1(S) and/or F2(t) could be zero.

Now since the both S and t are parameterized, also penalty function can be written in the form F(p1, p2, ..., pN, s1, s2, ..., sK). Now the automatic, determination of the best center surface and thickness function takes the form of minimization problem for objective function F over parameter space. There are many well-known algorithmic approaches for solving that minimization problem by a computer, such as a Powell & Brent or Gaussian method, for example.

A shape (and angle or location) of the surface S can be varied changing the parameters or the control points in the function F(St). Moreover by determining sharpness values for the panoramic layer maximizing the contrast of the adjacent pixels and changing also the parameters of the function the desired shape of the surface S and the panoramic layer can be obtained so that the shape of the surface S and the panoramic layer adapt to the geometry of the dentition or jaws of the patient and also sharp layer and great contrast for the panoramic image is achieved. The aforementioned steps are advantageously done automatically according to the present invention, whereupon the sharp panoramic layer is advantageously encouraged to follow the geometry of an anatomic-shape, such as a neural canal or jawbone, for example.

It should be noted that getting a sharp panoramic layer of the jaw neural canal is extremely difficult or even impossible according to the methods of known prior art because the neural canal in the jaw and thus also the sharpness area is very narrow. However, according to the present invention the sharp panoramic layer following the shape of the jaw neural canal is quite easy to obtain because of the contrast difference between the pixels of the neural canal and the surroundings of the neural canal, whereupon the changing of the parameters of the penalty function F(S,t) can be done very accurately so that the shape of the panoramic layer can be encouraged to follow the shape of the jaw neural canal.

Furthermore it should be noted that according to the present invention a certain sharp panoramic layer for the whole jaw can be determined, but also a certain part of the law area can be determined, such as a sector of a certain tooth or the root of the tooth, for example. Moreover it should be noted that according to the invention the panoramic layer image can be determined for a certain depth in the direction of t.

The invention offers also other clear advantages over the known prior art. Firstly one can determine number of sharp panoramic layer images at different depth (in direction of t) from image data obtained by one shot. Further the positioning of the patient is not so accurate than in methods of the prior art, and thus the method according to the present invention is easier and faster than the methods of known prior art. Especially, when comparing to the methods of the prior art, the present invention is very accurate and effective to determine a sharp panoramic image layer in the area of the front teeth, because the thickness area in the area of the front teeth is very narrow and thus the positioning of the patient according to the methods known from the prior art is extremely difficult, sometime even impossible. Moreover a radiation dose the patient is exposed to can be minimized by the invention, because number of different sharp panoramic layer images can be achieved by image data taken by only one shot.

As a conclusion it can be said that the main purpose of the present invention is to determine a penalty function to a panoramic image layer, minimizing the penalty function by changing parameters of the function and thus obtaining the better panoramic image layer the smaller the penalty function is, and also get the greater contrast and greater sharpness to the panoramic image layer.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
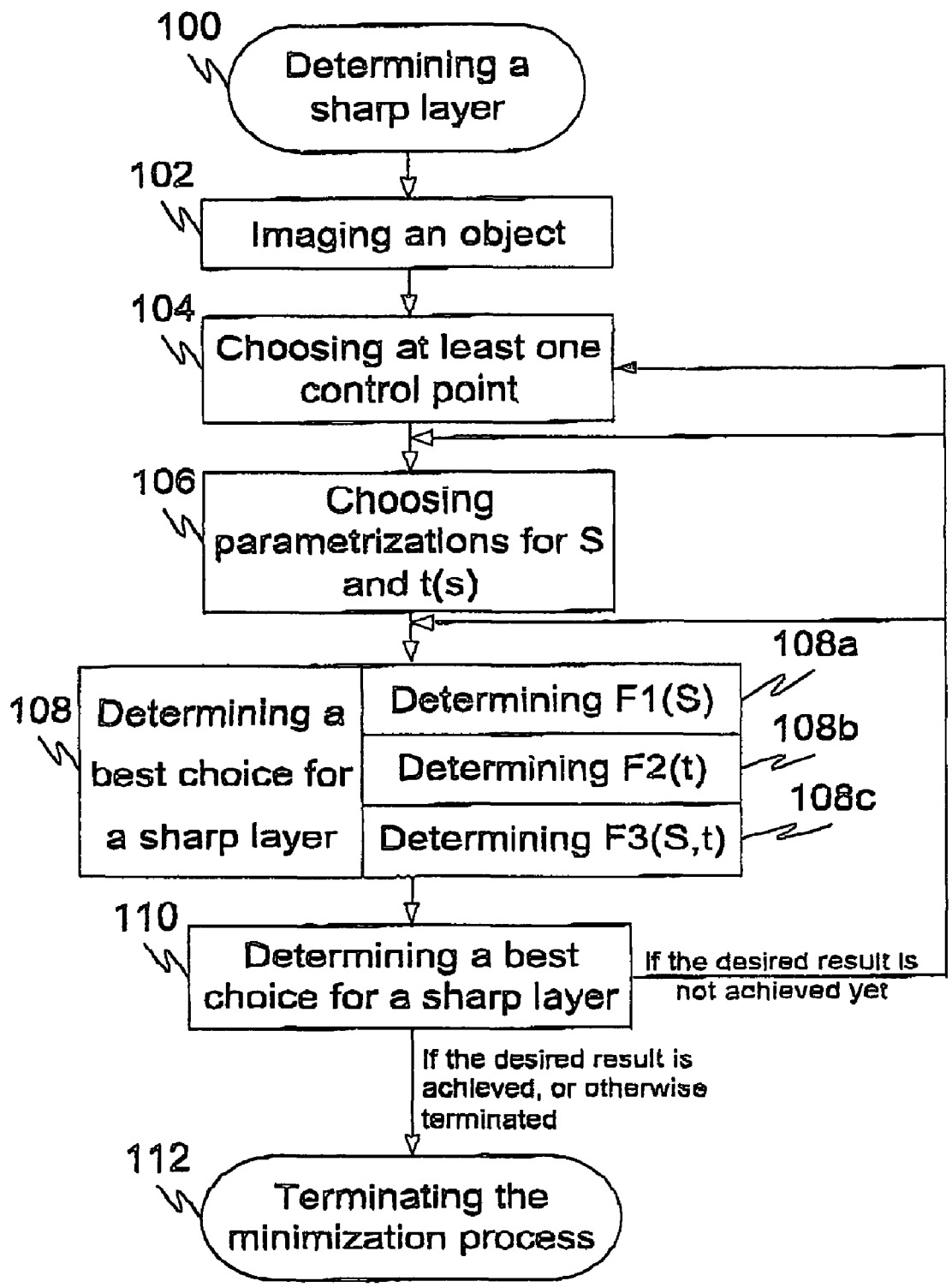
FIG. 1 illustrates a flow diagram of an exemplary method for determining a sharp panoramic image layer constructed from a group of projection images according to an advantageous embodiment of the present invention.

FIG. 1 illustrates a flow diagram of an exemplary method 100 for determining a sharp panoramic image layer constructed from a group of projection images according to an advantageous embodiment of the present invention, where at step 102 an object to be determined is imaged and numbers of projection images are obtained. Next at step 104 control points, or at least one control point, are chosen, and at step 106 parameterizations for a surface S and thickness function t(s) are chosen. Typically the points are located inside the dental arch, so that the distance between neighbouring points is typically between 10 mm-50 mm but it is not restricted to this distance scala.

Once the parameterizations of S and t(s) are chosen, the first best choice for a center surface of a sharp layer is determined at step 108 by defining a penalty function F(S,t), where F(S,t)=F1(S)+F2(*t*)+F3(S,t), for example. At step 108 the components of F(S,t), in other words F1(S), F2(*t*) and F3(S,t) are determined. To be exact at step 108*a* F1(S) is determined penalizing changes in the surface S, advantageously high-frequency changes. At step 108*b* F2(*t*) is determined penalizing changes in the thickness function t(S), advantageously high-frequency changes. Finally at step 108*c* F3(S,t) is determined. F3(S,t) computes first the panoramic image corresponding to the choices S and t(S) given as argument, and then penalizes low-frequency images more than high-frequency images of said computed panoramic image. However, it should be noted, that determining F1(S) and/or F2(*t*) can be optional (or the value of F1(S) and/or F2(*t*) can be zero), whereupon F(S,t)=F3(S,t), or F(S,t)=F1(S)+F3(S,t), or F(S,t)=F2(*t*)+F3(S,t). In the case, where F1(S) and F2(*t*) are determined (and F1(S)≠0≠F2(*t*)), F(S,t)=F1(S)+F2(*t*)+F3(S,t).

Now the determination 110 of the best center surface and thickness function takes the form of minimization problem for objective function F over parameter space. In the minimization process the parameters and control points can be changed at steps 104-108*c*. The minimization process may be completed for example, when a certain aforementioned sharpness is achieved, or otherwise the minimization process is terminated at step 112.

It should be noted that the order of steps 104-110 illustrated in FIG. 1 is exemplary and the steps 104-110 can also be performed in other order and also more than once before the desired result is achieved. Especially the solution for the minimization problem may takes number of steps to change parameters, control points, redetermining the components F1(S), F2(*t*), and F3(S,t) of the penalty function, for example, and determining a best choice for the sharp layer.

Figure 2:
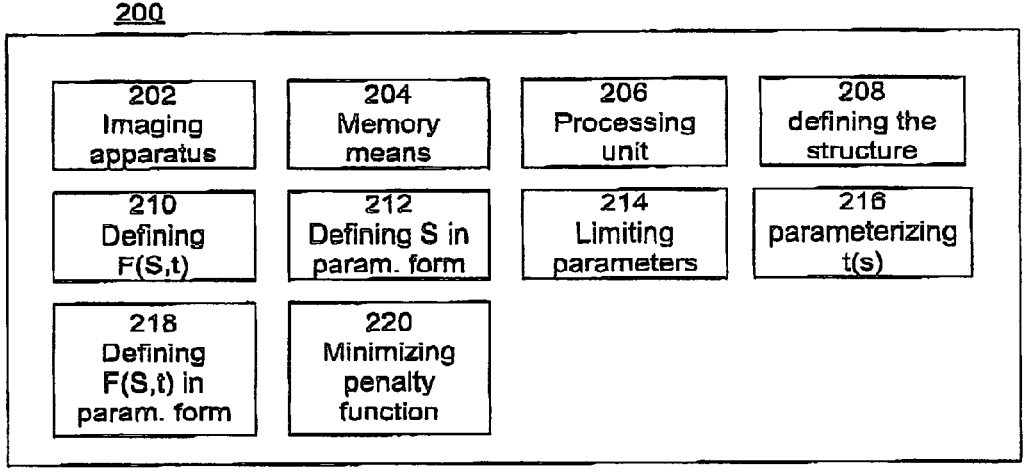
FIG. 2 illustrates a block diagram of an exemplary system for determining a sharp panoramic image layer constructed from a group of projection images according to an advantageous embodiment of the present invention.

FIG. 2 illustrates a block diagram of an exemplary system 200 for determining a sharp panoramic image layer constructed from a group of projection images according to an advantageous embodiment of the present invention, where the system comprises an imaging apparatus 202, such as an X-ray imaging device, memory means 204 for storing image data, processing unit 206 for processing image data for example, means 208 for defining the structure of the panoramic image by at least two crucial parameters, the first parameter relating to the central surface S of the sharp layer and the second parameter relating to the thickness t(s) of the sharp layer, and means 210 for defining a penalty function F(S,t) to obtain the best choice for a center surface and thickness function by minimizing said penalty function F(S,t) over parameter space, where said penalty function F(S,t) is sum of F1(S), F2(*t*) and F3(S,t), where F1(S) penalizes changes in the surface S (advantageously high-frequency changes). F2(*t*) penalizes changes in the thickness function t(S) (advantageously high-frequency changes), and F3(S,t) computes first the panoramic image corresponding to the choices S and t(S) given as argument, and penalizes low-frequency images more than high-frequency images of said computed panoramic image.

Further the system 200 advantageously comprises means 212 for defining the surface S in a parametric form: S(p1, p2, ..., pN), where p1, p2, ..., pN are real valued parameters so that said parameters determine the shape (and possibly also an angle or location) of the surface S. Advantageously said parameters are coordinates of a collection of control points (x1, y1, z1), (x2, y2, z2), ..., (xM, yM, zM) in a three dimensional space, and the surface S is made up, for example by said means 212, of spline functions passing through said control points. The system 200 may also comprise means 214 for limiting said parameter values advantageously from above and below in such a way that for all possible choices of the parameters, the corresponding surface S is realized with a panoramic X-ray device used to obtain the projection images.

Further the system 200 advantageously comprises means 216 for parameterizing the thickness function t(s) to the parameterization of S: write t(s1, s2, ..., sK), where s1, s2, ..., sK is a collection of points on the surface S. Moreover the system comprises also means 218 for defining the penalty function F(S,t) in a form F(p1, p2, ..., pN, s1, s2, ..., sK). The system comprises also means 220 for minimizing said penalty function using a Powell & Brent or Gaussian method, for example.

It should be noted, that at least part of means 208-220 can be integrated in said processing unit, which may be a microprocessor known from a prior art or a computer, for example.

Figure 3:
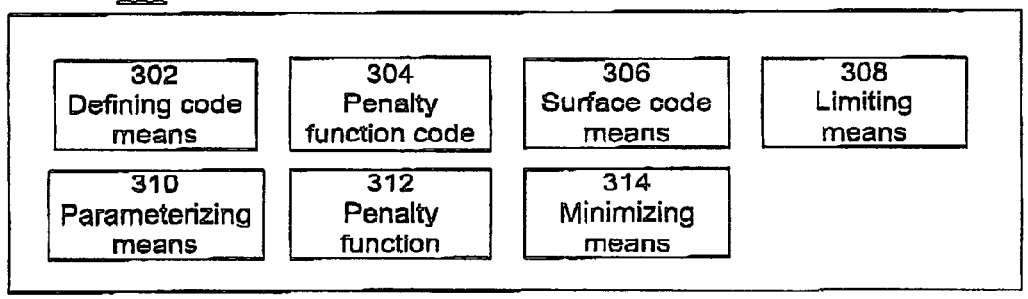
FIG. 3 illustrates an exemplary computer program product for determining a sharp panoramic image layer constructed from a group of projection images according to an advantageous embodiment of the present invention.

FIG. 3 illustrates an exemplary computer program product 300 for determining a sharp panoramic image layer constructed from a group of projection images according to an advantageous embodiment of the present invention, where the computer program product 300 is adapted to perform advantageously at least part of steps 104-112 of the method illustrated in FIG. 1, when the computer program product is run on a data processing unit 206, such as a computer.

Especially the computer program product 300 comprises defining code means 302, which is adapted to define the structure of the panoramic image by at least two crucial parameters, the first parameter relating to the central surface S of the sharp layer and the second parameter relating to the thickness t(s) of the sharp layer, when said defining code means is run on the data processing unit 206, and also penalty function code means 304, which is adapted to define a penalty function F(S,t) to obtain the best choice for a center surface and thickness function by minimizing said penalty function F(S,t) over parameter space, where said penalty function F(S, t) is sum of F1(S), F2(*t*) and F3(S,t), where F1(S) penalizes changes in the surface S (advantageously high-frequency changes), F2(*t*) penalizes changes in the thickness function t(S) (advantageously high-frequency changes), and F3(S,t) computes first the panoramic image corresponding to the choices S and t(S) given as argument, and penalizes low-frequency images more than high-frequency images of said computed panoramic image, when said penalty function code means 304 is run on the data processing unit.

Further the computer program product 300 advantageously comprises code means 306 for defining the surface S in a parametric form: S(p1, p2, ..., pN), where p1, p2, ..., pN are real valued parameters so that said parameters determine the shape and angle of the surface S, when said code means 306 is run on the data processing unit. Advantageously said parameters are coordinates of a collection of control points (x1, y1, z1), (x2, y2, z2), ..., (xM, yM, zM) in a three dimensional space, and the surface S is made up, for example by said means 306, of spline functions passing through said control points. The computer program product 300 may also comprise means 308 for limiting said parameter values advantageously from above and below in such a way that for all possible choices of the parameters, the corresponding surface S is realized with a panoramic X-ray device used to obtain the projection images, when said code means 308 is run on the data processing unit.

Further the computer program product 300 advantageously comprises means 310 for parameterizing the thickness function t(s) to the parameterization of S: write t(s1, s2, ..., sK), where s1, s2, ..., sK is a collection of points on the surface S, when said code means 310 is run on the data processing unit. Moreover the computer program product 300 comprises also means 312 for defining the penalty function F(S,t) in a form F(p1, p2, ..., pN, s1, s2, ..., sK). The computer program product 300 comprises also means 314 for minimizing said penalty function using a Powell & Brent or Gaussian method, for example, when said code means 306 is run on the data processing unit.

Figure 4:
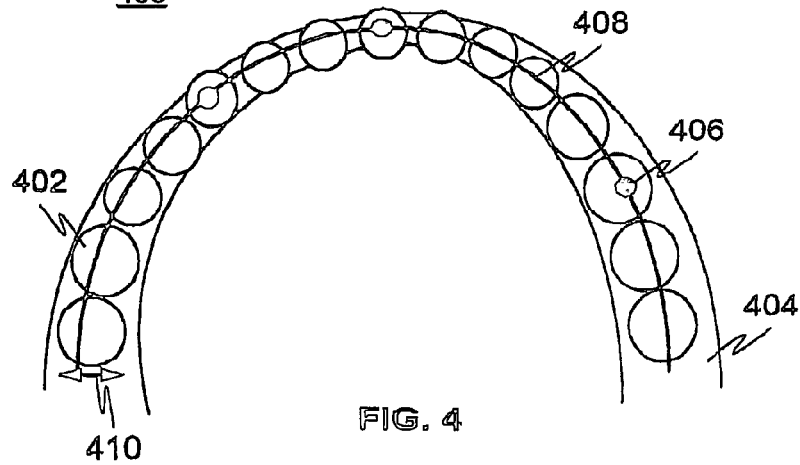
FIG. 4 illustrates a schematic view of an area of a dentition and of jaws and control points and surface S according to an advantageous embodiment of the present invention.

FIG. 4 illustrates a schematic view 400 of an area of a dentition 402 and of jaws 404 and control points 406 and a surface S 408 according to an advantageous embodiment of the present invention. In the invention the control points 406 are used as the points, through which the surface S 408 is fitted to pass. In addition to the surface S, also a thickness t(s) 410 of the sharp layer can be used to determine the structure of a panoramic image generated from a group of projection images.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. Especially it should be noted that the sharp panoramic image layer can be obtained also from image data using only term F3 in the penalty function.

The invention claimed is:

1. A method for determining a sharp layer from a sharp panoramic image layer generated by limited angle tomography, the sharp panoramic image layer extending along a clinically relevant curvilinear anatomic structure including a structure of a dentition jaw or jaw bone, the sharp panoramic image layer constructed from projection image data, the method comprising:
   operating an X-ray imaging device to obtain a plurality of projection images of the anatomic structure;
   configuring a non-transient storage medium wherein a set of computer executable code is stored;
   executing the set of computer executable code with a processor to carry out the following steps:
   identifying a first plurality of control points of a first thickness value of the sharp panoramic image layer;
   applying a penalty function to the first plurality of control points and the first thickness value;
   selecting a control point from the first plurality of control points that has a lowest penalty function value;
   identifying a second plurality of control points of a second thickness value of the sharp panoramic image layer;
   applying the penalty function to the second plurality of control points and the second thickness value;
   selecting a control point from the second plurality of control points that has a lowest penalty function value; and
   selecting a center surface (S) from a plurality of predetermined center surfaces as the sharp layer, the sharp layer being the center surface (S) that best fits the selected control points from the first and second plurality of control points.

2. The method of claim 1, wherein the penalty function computes a panoramic image corresponding to a plurality of control points and a thickness value, and wherein the penalty function computes a penalty that is inversely related to a frequency of data in the computed panoramic image.

3. The method of claim 2, wherein the penalty function computes a first panoramic image corresponding to the first plurality of control points and the first thickness value and computes a second panoramic image corresponding to the second plurality of control points and the second thickness value.

4. The method of claim 2, wherein the penalty function further computes the penalty as inversely related to a rate of change in a surface defined by the plurality of control points.

5. The method of claim 2, wherein the penalty function further computes the penalty as inversely related to a rate of change in the first thickness value or the second thickness value.

6. The method of claim 1, wherein the penalty function is a summation of F1(S), F2(t), and F3(S,t), and the step of applying the penalty function to the first plurality of control points comprises:
   calculating F1(S) as a value inversely related to a rate of change in the first plurality of control points;
   calculating F2(t) as a value inversely related to a rate of change in the first thickness value;
   calculating F3(S,t) as a value inversely related to a frequency of data in a first panoramic image constructed from the first plurality of control points and the first thickness value; and
   calculating a summation of F1(S), F2(t), and F3(S,t) as a penalty function value.

7. The method of claim 6, wherein the step of applying the penalty function to the second plurality of control points comprises:
   calculating F1(S) as a value inversely related to a rate of change in the second plurality of control points;
   calculating F2(t) as a value inversely related to a rate of change in the second thickness value;
   calculating F3(S,t) as a value inversely related to a frequency of data in a second panoramic image constructed from the second plurality of control points and the second thickness value; and
   calculating a summation of F1(S), F2(t), and F3(S,t) as a penalty function value.

8. The method of claim 1, wherein the sharp panoramic image layer is an X-ray image of a dentition or jaw.

9. The method of claim 1, wherein the first thickness value and the second thickness value are each within a range of 2 mm to 30 mm.

10. The method of claim 1, wherein the first plurality of control points and the second plurality of control points are coordinates in three dimensional space.

11. The method of claim 10, wherein the center surface (S) is made up of spline functions passing through the selected control points from the first and second plurality of control points.

12. The method of claim 11, wherein the first plurality of control points and the second plurality of control points are bounded by a dimension of the curvilinear anatomic structure in the plurality of projection images.

13. The method of claim 2, wherein the step of selecting the center surface (S) further comprises using a Powell & Brent or Gaussian method.

14. A system for determining a sharp layer from a sharp panoramic image layer generated by limited angle tomography, the sharp panoramic image layer extending along a clinically relevant curvilinear anatomic structure including a structure of a dentition jaw or jaw bone, the sharp panoramic image layer constructed from projection image data, the system comprising:
   an X-ray imaging device configured to obtain a plurality of projection images of the anatomic structure;
   a non-transient storage medium upon which a set of computer executable code is stored;
   a processor communicatively connected to the non-transient storage medium;
   wherein the processor performs the following steps upon execution of the set of computer executable code:
   identifying a first plurality of control points of a first thickness value of the sharp panoramic image layer;

applying a penalty function to the first plurality of control points and the first thickness value;

selecting a control point from the first plurality of control points that has a lowest penalty function value;

identifying a second plurality of control points of a second thickness value of the sharp panoramic image layer;

applying the penalty function to the second plurality of control points and the second thickness value;

selecting a control point from the second plurality of control points that has a lowest penalty function value; and selecting a center surface (S) from a plurality of predetermined center surfaces as the sharp layer, the sharp layer being the center surface (S) that best fits the selected control points from the first and second plurality of control points.

15. The system of claim 14, wherein the penalty function computes a panoramic image corresponding to a plurality of control points and a thickness value, and wherein the penalty function computes a penalty that is inversely related to a frequency of data in the computed panoramic image.

16. The system of claim 15, wherein the penalty function computes a first panoramic image corresponding to the first plurality of control points and the first thickness value and computes a second panoramic image corresponding to the second plurality of control points and the second thickness value.

17. The system of claim 15, wherein the penalty function further computes the penalty as inversely related to a rate of change in a surface defined by a plurality of control points.

18. The system of claim 15, wherein the penalty function further computes the penalty as inversely related to a rate of change in the first thickness value or the second thickness value.

19. The system of claim 14, wherein the penalty function is a summation of F1(S), F2($t$), and F3(S,t), and the processor applying the penalty function to the first plurality of control points comprises:

calculating F1(S) as a value inversely related to a rate of change in the first plurality of control points;

calculating F2($t$) as a value inversely related to a rate of change in the first thickness value;

calculating F3(S,t) as a value inversely related to a frequency of data in a first panoramic image constructed from the first plurality of control points and the first thickness value; and calculating a summation of F1(S), F2($t$), and F3(S,t) as a penalty function value.

20. The system of claim 19, wherein the processor applying the penalty function to the second plurality of control points comprises:

calculating F1(S) as a value inversely related to a rate of change in the second plurality of control points;

calculating F2($t$) as a value inversely related to a rate of change in the second thickness value;

calculating F3(S,t) as a value inversely related to a frequency of data in a second panoramic image constructed from the second plurality of control points and of second thickness value; and calculating a summation of F1(S), F2($t$), and F3(S,t) as a penalty function value.

21. The system of claim 14, wherein the first plurality of control points and the second plurality of control points are coordinates in three dimensional space.

22. The system of claim 14, wherein the center surface (S) is made up of spline functions passing through the selected control points from the first and second plurality of control points.

23. The system of claim 14, wherein the plurality of first control points and the plurality of second control points are bounded by a dimension of the curvilinear anatomic structure in the plurality of projection images.

24. A non-transient computer readable medium embodying computer readable code for determining a sharp layer from a sharp panoramic image layer generated by limited angle tomography, the sharp panoramic image layer extending along a clinically relevant curvilinear anatomic structure including a structure of a detention jaw or jaw bone, the sharp panoramic image layer constructed from projection image data, wherein upon execution of the computer readable code, the processor:

receives a plurality of projection images of the anatomic structure;

identifies a first plurality of control points of a first thickness value of the sharp panoramic image layer;

applies a penalty function to the first plurality of control points and the first thickness value;

selects a control point from the first plurality of control points that has a lowest penalty function value;

identifies a second plurality of control points of a second thickness value of the sharp panoramic image layer;

applies the penalty function to the second plurality of control points and the second thickness value;

selects a control point from the second plurality of control points that has a lowest penalty function value; and selects a center surface (S) from a plurality of predetermined center surfaces as the sharp layer, the sharp layer being the center surface (S) that best fits the selected control points from the first and second plurality of control points.

25. The computer readable medium of claim 24, wherein the penalty function computes a panoramic image corresponding to a plurality of control points and a thickness value, and wherein the penalty function computes a penalty that is inversely related to a frequency of data in the panoramic image.

26. The computer readable medium of claim 25, wherein the penalty function computes a first panoramic image corresponding to the first plurality of control points and the first thickness value and computes a second panoramic image corresponding to the second plurality of control points and the second thickness value.

27. The computer readable medium of claim 25, wherein the penalty function further computes the penalty as inversely related to a rate of change in a surface defined by the plurality of control points.

28. The computer readable medium of claim 25, wherein the penalty function further computes the penalty as inversely related to a rate of change in the first thickness value or the second thickness value.

29. The computer readable medium of claim 24, wherein the penalty function is a summation of F1(S), F2($t$), and F3(S,t), and the execution of the computer readable code further causes the processor to:

calculate F1(S) as a value inversely related to a rate of change in the first plurality of control points;

calculate F2($t$) as a value inversely related to a rate of change in the first thickness value;

calculate F3(S,t) as a value inversely related to a frequency of data in a first panoramic image constructed from the first plurality of control points and the first thickness value; and calculate a summation of F1(S), F2($t$), and F3(S,t) as a penalty function value.

* * * * *